United States Patent

Kauffman

(10) Patent No.: US 8,187,455 B2
(45) Date of Patent: May 29, 2012

(54) VOLTAMMETRIC TECHNIQUE TO DETERMINE THE INDIVIDUAL CONCENTRATION OF DIFFERENT ANTIOXIDANTS OF THE SAME CLASS

(75) Inventor: Robert E. Kauffman, Centerville, OH (US)

(73) Assignee: Socomer NV., Machelen (BE)

( * ) Notice: Subject to any disclaimer, the term of this patent is extended or adjusted under 35 U.S.C. 154(b) by 984 days.

(21) Appl. No.: 12/175,844

(22) Filed: Jul. 18, 2008

(65) Prior Publication Data

US 2010/0012529 A1    Jan. 21, 2010

(51) Int. Cl.
*G01N 27/26*    (2006.01)
*G01N 33/30*    (2006.01)

(52) U.S. Cl. ............ 205/787; 205/775; 205/775.5; 508/392; 73/114.55; 73/114.56; 73/53.05; 73/61.41

(58) Field of Classification Search .......... 205/787, 205/775, 775.5; 508/392; 73/114.55, 114.56, 73/56, 53.05, 61.41
See application file for complete search history.

(56) References Cited

U.S. PATENT DOCUMENTS

| 3,920,397 | A | * | 11/1975 | Small et al. ............ 436/79 |
|---|---|---|---|---|
| 4,032,555 | A | | 6/1977 | Bottaccio et al. |
| 4,744,870 | A | | 5/1988 | Kauffman |
| 4,764,258 | A | * | 8/1988 | Kauffman ............ 205/786 |
| 4,908,322 | A | * | 3/1990 | Jacobson et al. ............ 436/111 |
| 5,071,527 | A | | 12/1991 | Kauffman |
| 5,239,258 | A | | 8/1993 | Kauffman |
| 5,480,808 | A | | 1/1996 | Kauffman et al. |
| 5,770,038 | A | | 6/1998 | Iwama et al. |
| 6,217,745 | B1 | | 4/2001 | Fang |
| 6,255,954 | B1 | | 7/2001 | Brown et al. |
| 6,429,021 | B1 | | 8/2002 | Qian et al. |
| 6,638,415 | B1 | | 10/2003 | Hodges et al. |
| 7,043,967 | B2 | | 5/2006 | Kauffman et al. |
| 2007/0004602 | A1 | * | 1/2007 | Waynick ............ 508/392 |
| 2007/0129268 | A1 | * | 6/2007 | Bell et al. ............ 508/545 |

OTHER PUBLICATIONS

Koehler Ruler Sales Training Manual 2001.*
Ruler Operations Manual 2005.*
R.E. Kauffman, "Development of a Remaining Useful Life of a Lubricant Evaluation Technique. Part III. Cyclic Voltammetric Techniques." Lub. Eng. 1989., 45, pp. 709-716.

* cited by examiner

*Primary Examiner* — Jeffrey T Barton
*Assistant Examiner* — Jennifer Dieterle
(74) *Attorney, Agent, or Firm* — Lowenstein Sandler PC

(57) ABSTRACT

Disclosed in certain embodiments is a method of determining the individual concentration of different antioxidants of the same class in a sample comprising contacting the sample with an effective amount of phenol; and analyzing the sample by voltammetry.

5 Claims, 8 Drawing Sheets

VOLTAMMETRIC TECHNIQUE TO DETERMINE THE INDIVIDUAL CONCENTRATION OF DIFFERENT ANTIOXIDANTS OF THE SAME CLASS

STATEMENT REGARDING REFERENCES

All patents, publications, and non-patent references referred to herein are incorporated by reference in their entireties.

BACKGROUND OF THE INVENTION

Voltammetric analytical techniques are used to determine the antioxidant concentrations of a wide range of lubricating oils and greases as described in U.S. Pat. Nos. 4,744,870 and 4,764,258. U.S. Pat. No. 4,744,870 describes a cyclic voltammetric procedure for measuring the secondary aromatic amine antioxidant concentrations of ester based lubricating oils used in aircraft engines. U.S. Pat. No. 4,764,258 describes a linear sweep voltammetric procedure for measuring the concentrations of different type antioxidants such as sterically hindered phenols, alkyl amines, and zinc dialkyldithiophosphates (ZDDP) in petroleum based lubricating oils and greases. The linear sweep voltammetry is used in place of the cyclic voltammetry for the petroleum based oils because ZDDP, naturally occurring phenols, and other electrochemically active species cause electrode filming during the reductive cycle of the cyclic voltammetry analysis.

Although the voltammetric techniques are capable of differentiating between different classes of antioxidants (e.g., hindered phenols versus secondary aromatic amines), they are incapable of differentiating between different types of antioxidants of the same class (one peak produced by mixture of different amines). Until recently, the inability to distinguish between different amine antioxidants with similar structures was not a limitation since the different antioxidants and their oxidation products were highly soluble in the basestock used in the specific lubricating oil formulations.

However, environmental regulations and higher equipment operating temperatures have required changes in the basestock refining processes and traditional lubricant formulations. Specifically, highly refined petroleum basestocks with reduced sulfur and nitrogen contents and synthetic hydrocarbons are now being used in many lubricating oil formulations due to their superior thermal and oxidative stabilities compared to traditional petroleum basestocks. Also, secondary aromatic amine antioxidants are now being used in the refined petroleum and synthetic hydrocarbon basestocks of industrial turbine oils due to their higher temperature capabilities and in the basestocks of automotive and diesel engine oils to supplement the reduced levels of ZDDP.

In many of the applications, reports of lubricant related equipment damage and failures coincided with the introduction of the new oil formulations utilizing high purity basestocks and secondary amine antioxidants. In many instances, the insolubilities of the basestock oxidation products (varnish, unsaturated carboxylic acids) and secondary amine antioxidant by-products (sludge, aromatic amine dimers and trimers) were identified as the cause(s) of the lubricant related malfunctions. In addition to the solubility issues, the secondary aromatic amines are less effective antioxidants at lower temperatures than hindered phenols leading to increased rates of basestock oxidation, and consequently, increased amounts of varnish adhering to or clogging components with reduced clearances such as servo valves, bearings, filters, etc.

Previous research projects with cyclic voltammetry (see U.S. Pat. No. 4,744,870 and original RULLET Part III paper in Lub. Eng. Kauffman, R. E., (1990), "Development of a Remaining Useful Life of a Lubricant Evaluation Technique. Part III. Cyclic Voltainmetric Techniques," *Lubr. Eng.*, 46,1, pp 709-716) have shown that the tendencies of secondary aromatic amines to form insoluble dimers and trimers (sludge) are strongly related to chemical structure. When they are the sole antioxidant used in the oil formulation, sterically hindered aromatic amines such as p,p'-dioctyldiphenyl amine (DODPA) undergo reversible electro-oxidation/reduction during cyclic voltammetric analysis; successive oxidation/reduction cycles do not affect the composition of the DODPA molecule at the molecule surface (i.e. less likely to form sludge). In contrast, less hindered aromatic amines such as phenyl alpha naphthyl amine (PANA) and p-octylphenyl alpha naphthyl amine (Octyl-PANA) undergo irreversible electro-oxidation/chemical reactions to produce lower solubility aromatic amine polymers (sludge) which then undergo further electro-oxidation/reduction reactions. When DODPA and PANA combinations are used, irreversible electro-oxidation reactions occur to produce DODPA-PANA polymeric compounds (sludge).

Since the capability of a secondary aromatic amine antioxidant to undergo irreversible electro-oxidation during cyclic voltammetry is related to the antioxidant's chemical structure and tendency to form sludge during use in operating equipment, cyclic voltammetry potentially has both the capability of determining the individual secondary aromatic amine concentrations as well as the sludge tendencies of in-service oils. However, hindered (antioxidants) and unhindered (naturally occurring) phenols, ZDDP, and other compounds in the lubricating oil undergo irreversible electro-oxidation reactions forming insoluble polymer films on the electrode surface during cyclic voltammetric analyses making the technique impractical for fully formulated lubricating oils.

Thus, there exists a need for a voltammetric method by which to distinguish among different types of aromatic amine antioxidants of the same class.

SUMMARY OF THE INVENTION

It is an object of the present invention to provide a method for determining the individual concentration of different substances of the same class in a sample.

It is an object of certain embodiments of the present invention to provide a method for determining the individual concentration of different antioxidants of the same class in a sample.

It is an object of certain embodiments of the present invention to provide a method for determining the individual concentration of different antioxidants of the same class in lubricating oil.

It is an object of certain embodiments of the present invention to provide a method for determining soft body production processes o in-service lubricating oils.

The above objects of the invention, and others, can be achieved by the present invention, which in certain embodiments is directed to a method of determining the individual concentration of different antioxidants of the same class in a sample comprising contacting the sample with an effective amount of phenol; and analyzing the sample by voltammetry.

In further embodiments, the invention is directed to a method of analyzing an oil sample for acidic oxidation products and sludge comprising generating a first graphical representation by analyzing a solution of overbased phenate dissolved in alcohol using linear sweep voltammetry; adding an oil sample to the alcohol solution and analyzing the solution using linear sweep voltammetry to generate a second graphical representation; and comparing the graphical representations of the first and second graphical representations.

In other embodiments, the method further comprising adding an additional sample of oil to the solution one or more times to generate one or more additional graphical representations; and comparing the graphical representations.

In other embodiments, the present invention is directed to a method of analyzing an oil sample for acidic oxidation products and sludge by generating a baseline graphical representation using voltammetry and comparing it to a graphical representation of the sample after mixing the sample with overbased phenate.

In certain embodiments, the voltammetry is selected from cyclic voltammetry or linear sweep voltammetry.

In certain embodiments, phenol is produced in the sample in situ, e.g., by adding overbased phenate and an acid to the sample.

In alternative embodiments, the phenol is introduced directly into the sample, e.g., by mixing the overbased phenate and acid prior to incorporation in the sample.

In certain embodiments, the analyzing comprises measuring the peaks produced by the amines in the presence and absence of phenol.

In alternative embodiments, the analyzing further comprises generating a first graphical representation of the sample prior to contacting the sample with phenol; generating a second graphical representation of the sample after contacting the sample with phenol; and comparing the first and second graphical representation In other embodiments, the invention is directed to a kit comprising overbased phenate, acid and optionally any other useful component of the invention disclosed herein.

DETAILED DESCRIPTION OF THE INVENTION

Figure 1:
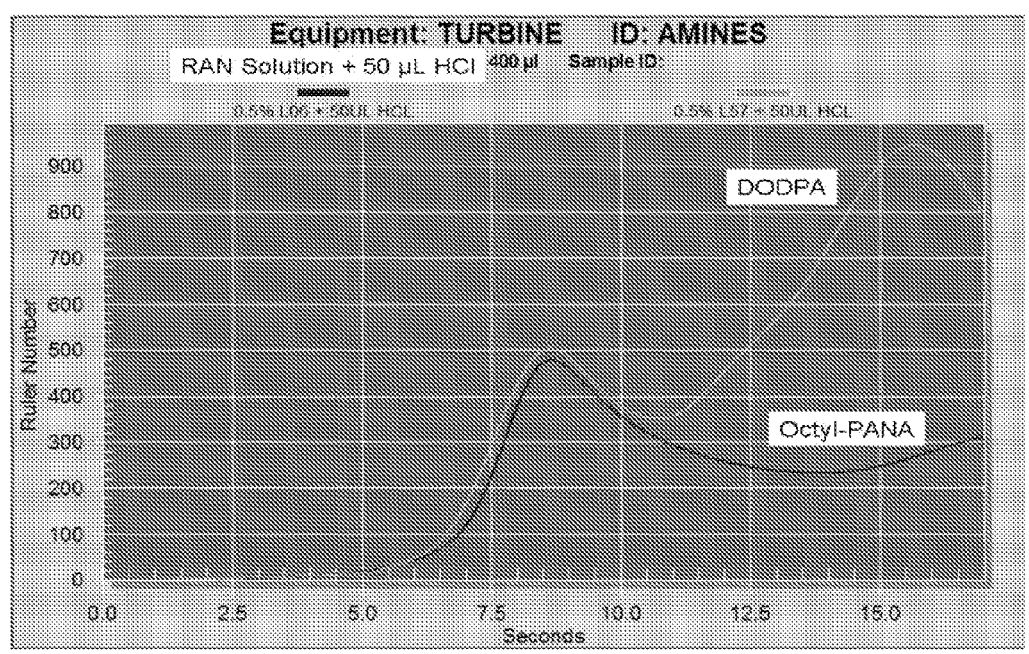
FIG. 1 depicts voltammograms of oils containing 0.5% Octyl-PANA and DODPA in alcoholic solution containing phenol generated in situ from excess sodium phenate.

By virtue of the present invention, a voltammetric technique has been developed to determine the individual concentrations of different antioxidants of the same class in a sample. Preferably, the sample is an oil such as a lubricating oil.

In a particular embodiment, the technique is directed to determine the individual concentrations of hindered antioxidants, e.g., DODPA and unhindered antioxidants, e.g., Octyl-PANA type amine antioxidants (as well as oxidation by-products of these antioxidants) utilizing linear sweep voltammetric technique. Linear voltammetric is a preferred technique as it is portable, easy to operate, suitable for on-site or laboratory use and is already in use for determining the total aromatic amine and phenol concentrations of lubricating oils. To differentiate the hindered and unhindered aromatic amines, and acid (e.g. hydrochloric acid, acetic acid, or phosphoric acid) are added to the voltammetric test solution to produce phenol in situ. The overbased phenate can be, e.g., Na+, Li+, and NR$_4$+ (wherein each R is independently H or a C$_{1-4}$ alkyl)phenate. The phenol moiety of the overbased phenate can also be substituted, e.g., with 1-5 substituents independently selected from the group consisting of alkyl, alkoxy or phenyl groups. One particular substituted phenate is sodium O-phenylphenate. The in situ generated phenol reacts with the secondary aromatic amines to change their electro-oxidation characteristics. Unhindered antioxidants such as octyl-PANA type amines do not undergo electro-oxidation and do not produce a peak or a substantial peak during voltammetric analysis. The hindered antioxidants such as DODPA type antioxidants undergo electro-oxidation at a higher voltage wherein the peak shifts to higher voltage (longer time) during voltametric analysis. The differences in the resultant peaks after reaction with phenols provides the opportunity to analyze the tested sample. For example, the sizes of the voltammetric peaks produced by the secondary aromatic amines in the absence (representing the total class) and presence (representing hindered antioxidant, e.g., DODPA) of the in situ generated phenol are measured and used to characterize the aromatic amine antioxidant systems of new oils and normal used oils.

In abnormal used oils containing acidic varnish compounds (oxidation by-products), phenol is added produced in situ upon the addition of sodium phenate resulting in a higher voltage peak for hindered antioxidants such as DOPA that are present in lubricating oil or added with phenate. In such an embodiment, the phenol can be produced in situ without the addition of an acid due to the acidic conditions due to the varnish compounds.

In abnormal used oils containing sludge compounds (antioxidant polymers), a lower voltage peak is produced upon the addition of sodium phenate due to the alkalinity of sodium phenate causing amine polymers to electro-oxidize at a lower voltage.

In producing phenol in situ, the phenol can be produced by adding overbased phenate and an acid to the sample. Alternatively, as discussed above, the phenol can be produced in situ with the addition of overbased phenate without an acid if the sample is sufficiently acidic to form phenol upon addition of the overbased phenol alone. In preferred embodiments, the overbased phenol is sodium phenate.

The acid utilized in the methods of the present invention can be any suitable acid that will react with the overbased phenate to produce phenol, such as inorganic or organic acids. Examples of suitable inorganic acids include but are not limited to hydrochloric acid, nitric acid, sulfuric acid, hydrofluoric acid, boric acid and phosphoric acid. Examples of organic acids include but are not limited to acetic acid, oxalic acid, maleic acid, formic acid, malonic acid, phthalic acid, fumaric acid, itaconic acid, succinic acid, mesaconic acid, citraconic acid, malic acid and glutaric acid.

In preferred embodiments, the methods of the invention are directed to determining the individual concentration of different antioxidants of the amine class. The antioxidants which are detected can be, e.g., hindered amines, unhindered amines or a combination thereof. The hindered amines can be, e.g., p,p'-dioctyldiphenyl and the unhindered amines can be, e.g., phenyl alpha naphthyl amine, p-octylphenyl alpha naphthyl amine, or a combination thereof.

The amount of phenol in the sample (either directly added or formed in situ) should be in an effective amount to react with the aromatic amines. In certain embodiments, the phenol is in an effective amount to react with hindered amines to form an electroactive compound and/or in an effective amount to react with unhindered amines to form a nonelectroactive compound.

In methods of forming the phenol in situ, the phenol can be produced, e.g., by mixing the sample with a solvent the overbased phenate, and the acid in any order. In a particular embodiment, however, the sample is added to an alcohol solution containing overbased phenate and the acid is added thereafter.

The solvent can be any suitable solvent such as an alcohol. The alcohol can be, e.g., methanol, ethanol, isopropanol, n-propanol, n-butanol and other isomers and mixtures thereof.

In such methods, the mixing can include, e.g., mixing from about 1.0 mL to about 10 mL of a solvent containing overbased phenate, from about 10 µL to 100 µL of an aqueous acid and from about 100 µL to about 800 µL of the sample.

The ratio of sample to solvent containing overbased phenate can be, e.g., from about 1:5 to about 1:25; the ratio of sample to aqueous acid can be, e.g., from about 1:4 to about 1:20; and the ratio of aqueous acid to solvent containing overbased phenate can be, e.g., from about 1:3 to about 1:15.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Octyl-PANA (Product L06 from Ciba) and DODPA (Product L57 from Ciba) were dissolved in petroleum basestocks (Group 1 or 2) to produce oils containing 0.5% antioxidant. The voltammograms in FIG. 1 were produced by dispensing 400 µL of oil into 5 mL of alcohol (ethanol) solution containing sodium phenate (0.05 molar shaking vial by hand, dispensing 50 µL of 2N aqueous HCl into the alcoholic solution to produce phenol from the sodium phenate in situ. The peak between 6 and 10 seconds in FIG. 1 is produced by the unreacted sodium phenate and indicates that the solution is still basic.

The voltammograms in FIG. 1 show that octyl-PANA did not produce a peak while DODPA produced a broad peak between 11 and 17 seconds, i.e., the produced phenol reacted with the unhindered octyl-PANA to form a compound that was not electroactive and/or polymeric (insoluble) and with sterically hindered DODPA to form a compound that was electroactive and soluble (50 µL of 2N aqueous HCl does not produce a peak in the 10 to 17 second region without the presence of DODPA).

Example 2

Octyl-PANA (Product L06 from Ciba) and DODPA (Product L57 from Ciba) were dissolved into petroleum basestocks (Group 1 or 2) to produce oils containing 0.5% antioxidant. One voltammogram in FIG. 2 (1.1 L06/L57PHCl) was produced by dispensing 200 µL of each oil into 5 mL of ethanol solution containing sodium phenate (0.05 molar), dispensing 200 µL of ethanol containing dodecylphenol (0.05 molar), hand shaking vial and then dispensing 50 µL of 2N aqueous HCl into the alcoholic solution containing sodium phenate to produce the reactive phenol in situ. The lower peak between 7.5 and 10 seconds (compared to 1:1 L06/L57PHENOL) is produced by the unreacted, sodium phenate and indicates that the solution is still basic.

Figure 2:
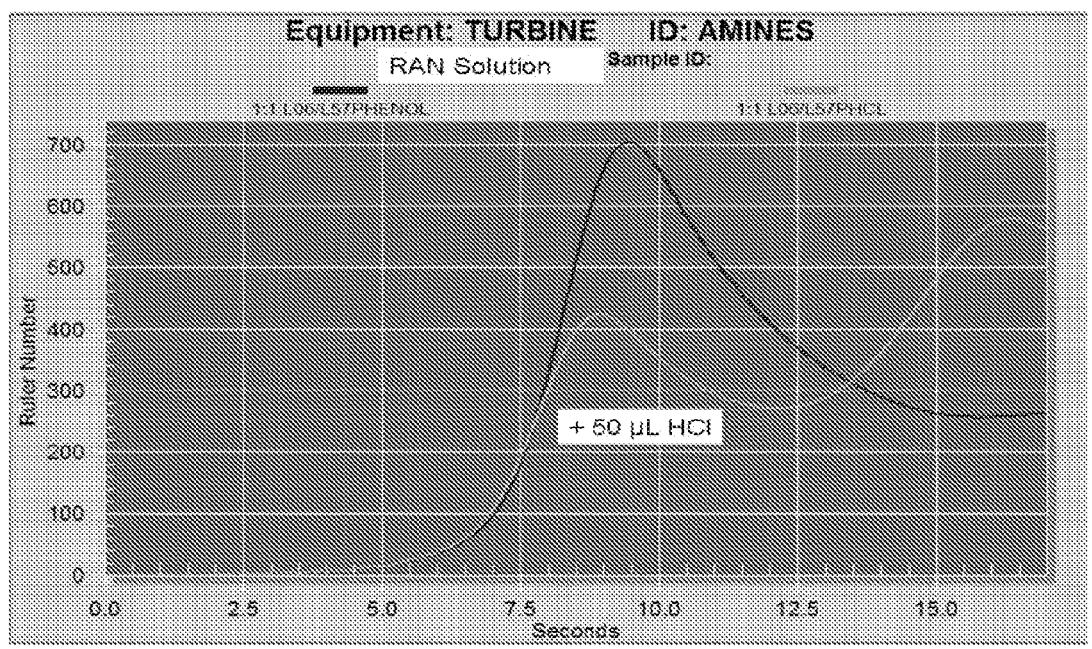
FIG. 2 depicts voltammograms of oils containing 0.5% Octyl-PANA, 0.5% DODPA and 0.5% dodecylphenol in alcoholic solution with and without phenol generated in situ from excess sodium phenate.

As in FIG. 1, the voltammogram in FIG. 2 (1:1 L06/L57PHCl) contains a broad peak between 11 and 17 seconds indicating DODPA produced a peak in the presence of the two phenols and excess sodium phenate. The other voltammogram in FIG. 2 (1:1 L06/L57PHENOL) was produced by dispensing 200 µL of each oil into 5 mL of alcohol (ethanol) solution containing sodium phenate (0.05 molar) followed by 200 µL of ethanol containing dodecylphenol (0.5%). No acid was added to produce phenol in situ. The higher peak between 7.5 and 10 seconds is produced by the original amount of added sodium phenate and indicates that the solution is highly basic.

In contrast to FIG. 1, the voltammogram in FIG. 2 (1:1 L06/L57PHENOL) does not contain a broad peak between 11 and 17 seconds indicating the DODPA and octyl-PANA do not produce a peak in the presence of the sterically hindered dodecylphenol and excess sodium phenate, i.e., the peak between 11 and 17 seconds is a reaction product of the DODPA with the sterically unhindered phenol.

Example 3

Octyl-PANA (Product L06 from Ciba) and DODPA (Product L57 from Ciba) were dissolved into petroleum basestocks (Group 1 or 2) to produce oils containing 0.5% antioxidant. All of the voltammograms shown in FIG. 3 were produced after dispensing 50 µL of 2N aqueous HCl into the alcoholic solutions containing sodium phenate to produce the reactive compound (phenol) in situ. The peaks between 7.5 and 10 seconds demonstrate that the remaining amount of unreacted sodium phenate was similar for each sample regardless of the amount of amine added and indicates that all of the solutions were basic.

Figure 3:
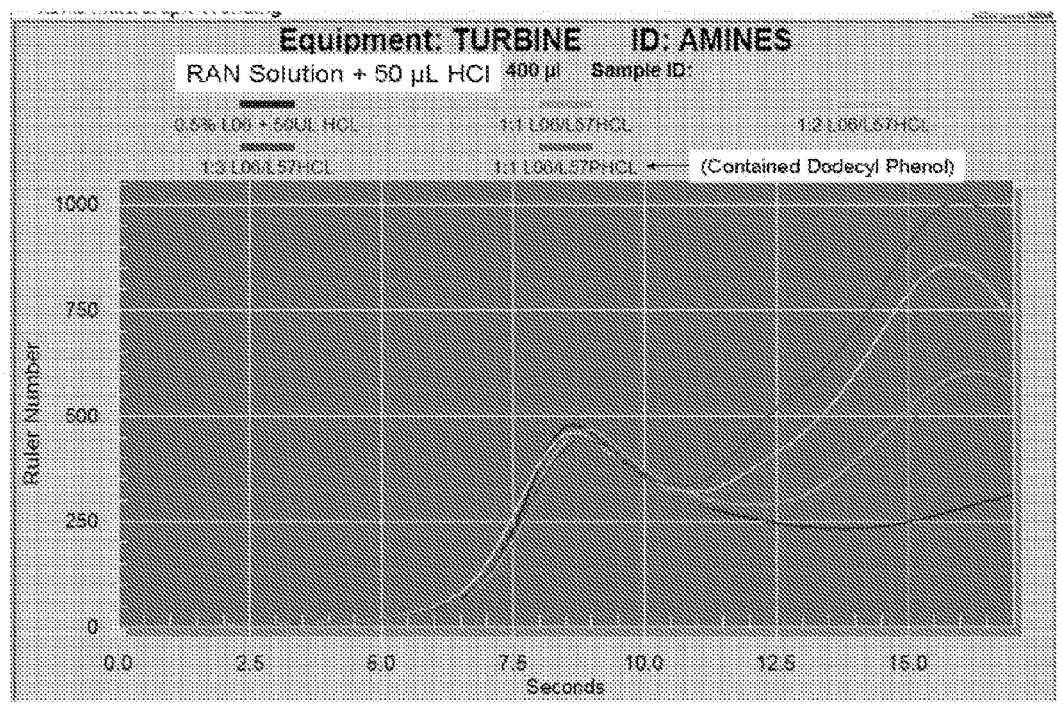
FIG. 3 depicts voltammograms of oils containing different concentrations of L06 (Octyl-PANA), L57 (DODPA) and dodecylphenol in alcoholic solution with phenol generated in situ from excess sodium phenate.

The lowest voltammogram in FIG. 3 was produced by dispensing 200 µL of the oil containing 0.5% L06 (octyl-PANA) into 5 mL of alcohol (ethanol) solution. As in FIG. 1, the L06 amine does not produce a broad peak between 11 and 17 seconds.

The middle two voltammograms were produced by dispensing 200 µL of each oil into the same 5 mL of alcohol (ethanol) solution before (1:1 L06/L57PHCl) and after (1:1 L06/L57PHCl) dispensing 200 µL of ethanol containing dodecylphenol (0.5%) into the oil/ethanol mixture. The voltammograms show that the presence of the sterically hindered dodecylphenol has no effect on the size of peak produced by the L57 (DODPA).

The upper two voltammograms in FIG. 3 were produced by dispensing 200 µL of the oil containing 0.5% L06 (octyl- PANA) into two different 5 mL of alcohol (ethanol) solutions and then dispensing 400 μL of the oil containing 0.5% L57 (DODPA) into one solution (1:2 L06/L57) and 600 μL of the oil containing 0.5% L57 into the other solution (1:3 L06/L57). The voltammograms in FIG. 3 show that the peak between 11 and 17 seconds produced by L57 (DODPA) increases with L57 concentration, i.e., the peak height/size is dependent on L57 concentration. Adding 400 μL of the oil containing 0.5% L06 to the solution containing 600 μL of 0.5% L57 had no effect on the peak size, i.e., peak height/size is independent of L06 (octyl-PANA) concentration.

Example 4

To demonstrate the relationships between basestock oxidation, amine type and soft body production (submicron varnish and sludge particles suspended in oil) of used oils, turbine oil samples from US and Europe were tested. The oil samples had previously been tested using Quantitative Spectrophotometric Analysis (QSA—oil filtered and color of filter inspected and related to levels of varnish/sludge circulating with oil) with QSA ratings ranging from 3 to 95 with 57-79 considered Abnormal and 80-100: Critical.

Used oil samples with QSA ratings of 3, 42, 60, 64, 73 and 95 representing samples with normal (3 and 42), abnormal (60, 64 and 73) and critical (95) varnish potential were analyzed in neutral acetone solution with linear sweep voltammetry to characterize the oils' amine and phenol antioxidant contents. Regardless of the QSA number, all of the samples have a single amine peak at 9 seconds in FIG. 4 even though different secondary amines are known to be present. Sample 42 has a substantial phenol peak at 14 seconds and sample 3 has a small peak at 5.5 seconds (area where amine dimers and trimers are detected).

Figure 5:
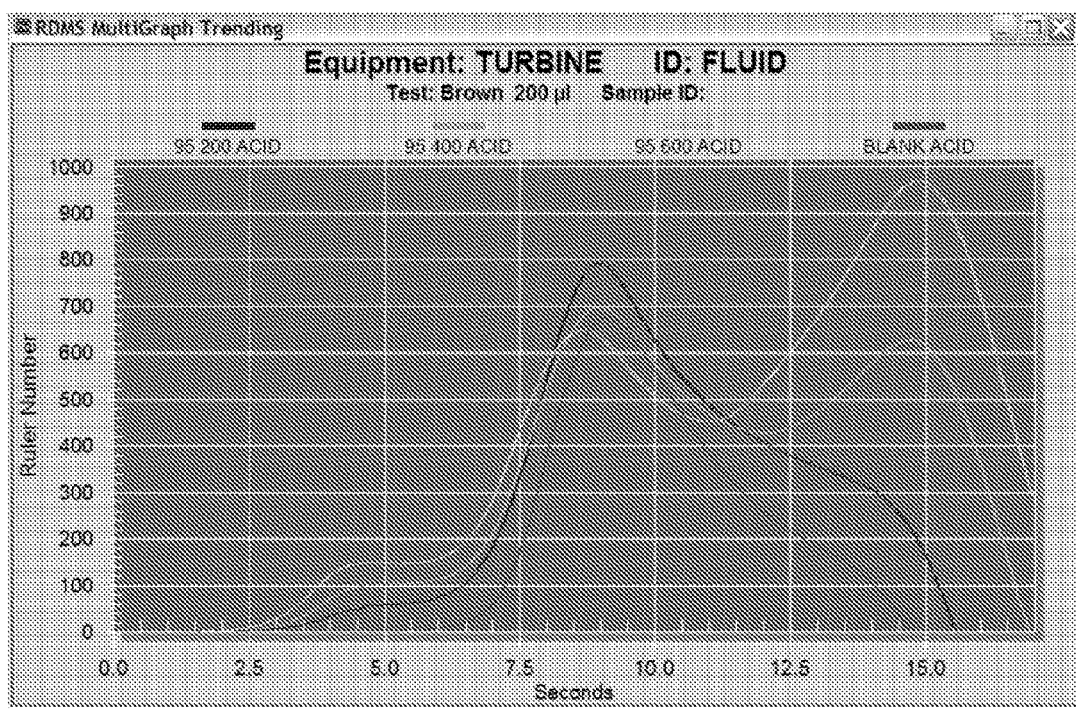
FIG. 5 depicts voltammograms of 200-600 μL of used turbine oil with QSA rating 95 added to sodium phenate in alcohol solution (no HCl added).

Since varnish particles (basestock oxidation) have been reported to be unsaturated carboxylic acids, the ethanol solutions containing sodium phenate were also used to analyze the turbine oil samples for both acidic oxidation products (reduction of sodium phenate peak) and sludge (peak at lower voltage than sodium phenate peak). Multiple linear sweep voltammetric analyses were run with each 5 mL ethanol solution containing sodium phenate as follows:

analyze solution to get baseline (large peak at 9 seconds in FIG. 5 due to unreacted sodium phenate)
add 200 μL of used oil, shake for 30 seconds, voltammetric analysis (200 ACID)
add additional 200 μL of oil, shake for 30 more seconds, voltammetric analysis (400 ACID)
add final 200 μL of oil, shake for another 30 seconds and voltammetric analysis with (600 ACID).

The three consecutive oil adds/analyses were performed to ensure the sodium phenate peak was stable, the test was valid over a range of oil amounts and any produced peaks increased with oil amount, i.e., related to concentration of species in used oil. The first sample analyzed was the 95 QSA sample since its critical rating indicated it would be the sample with the highest concentration of sludge/varnish particles. The 95 200 ACID voltammogram in FIG. 5 for the 200 μL sample size has a peak at 5 seconds and an increased sodium phenate peak compared to the baseline (phenate peak increase due to peak 3-6 seconds—assigned to amine antioxidant dimers (sludge) since hindered phenol antioxidant not detected in FIG. 4). The 200 ACID voltammogram in FIG. 5 has a shoulder at 13-15 seconds that becomes a well defined peak between 11-17 seconds as the sample size is increased to 600 μL as shown by the 95 600 ACID voltammogram in FIG. 5.

Figure 4:
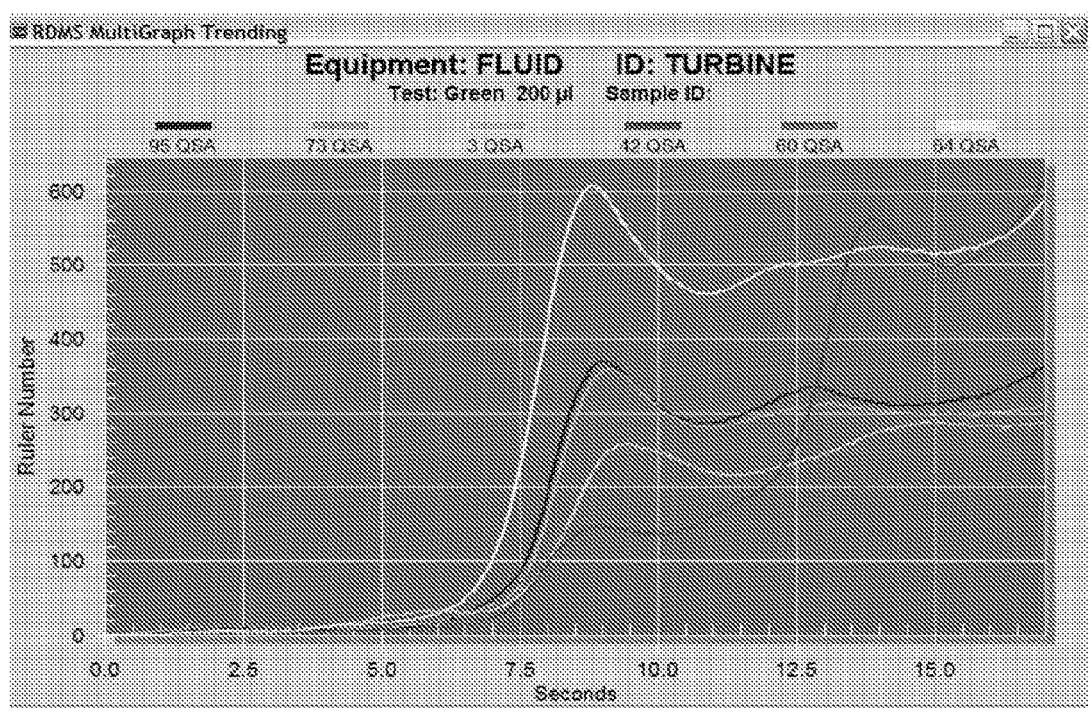
FIG. 4 depicts voltammograms of used turbine oils with QSA ratings ranging from 3 to 95 in neutral acetone.

Since the peak at 11 to 17 seconds is not present in FIG. 4, the peak is due to interaction of the phenol with a species in the used oil to produce an electroactive species (very similar to DODPA peak in FIG. 3, peak at 15 seconds instead of 16 seconds in FIG. 4). The presence of the 11-17 second indicates acidic components (carboxylic acids, varnish) are present in the 95 QSA sample (create phenol to react with DODPA type antioxidant). The peak due to the sodium phenate slowly decreases (after subtraction of dimer peak) with increasing used oil concentration, i.e., also indicates presence of acidic oxidation components in used oil.

Figure 6:
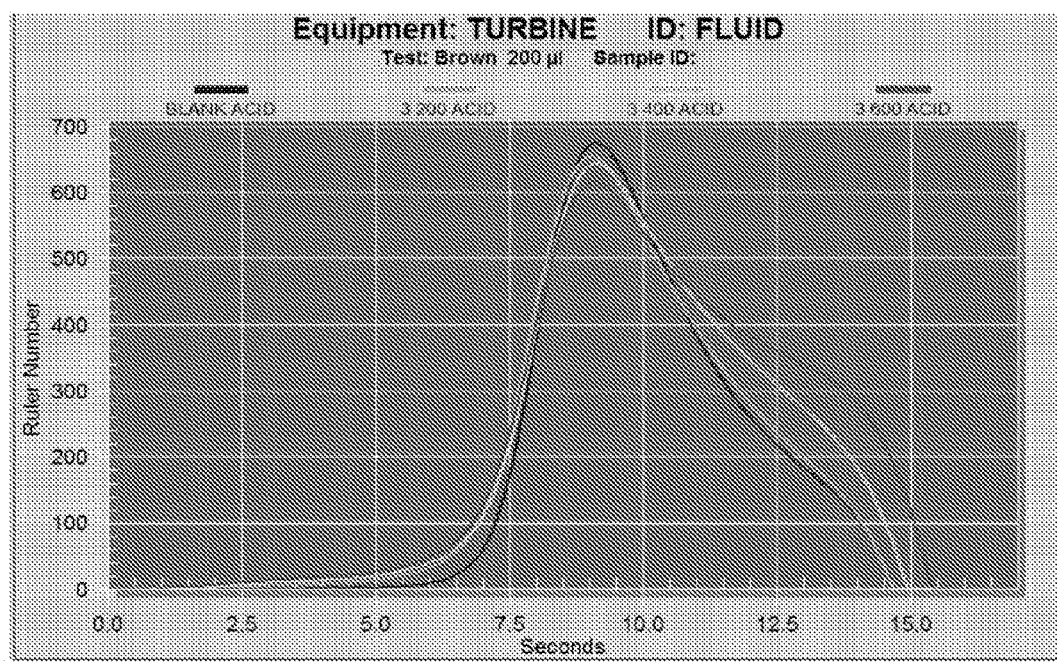
FIG. 6 depicts voltammograms of 200-600 μL of used turbine oil with QSA rating 3 added to sodium phenate in alcohol solution (no HCl added).

In contrast to the 95 QSA sample, the 3 QSA sample voltammograms in FIG. 6 do not contain a peak at 5 seconds (amine dimer) and only a small shoulder at 14 seconds after 600 μL of oil added (3 600 ACID in FIG. 6). The phenate peak at 9 seconds decreased only slightly with increasing oil amounts also indicating minimal acid levels.

Figure 7:
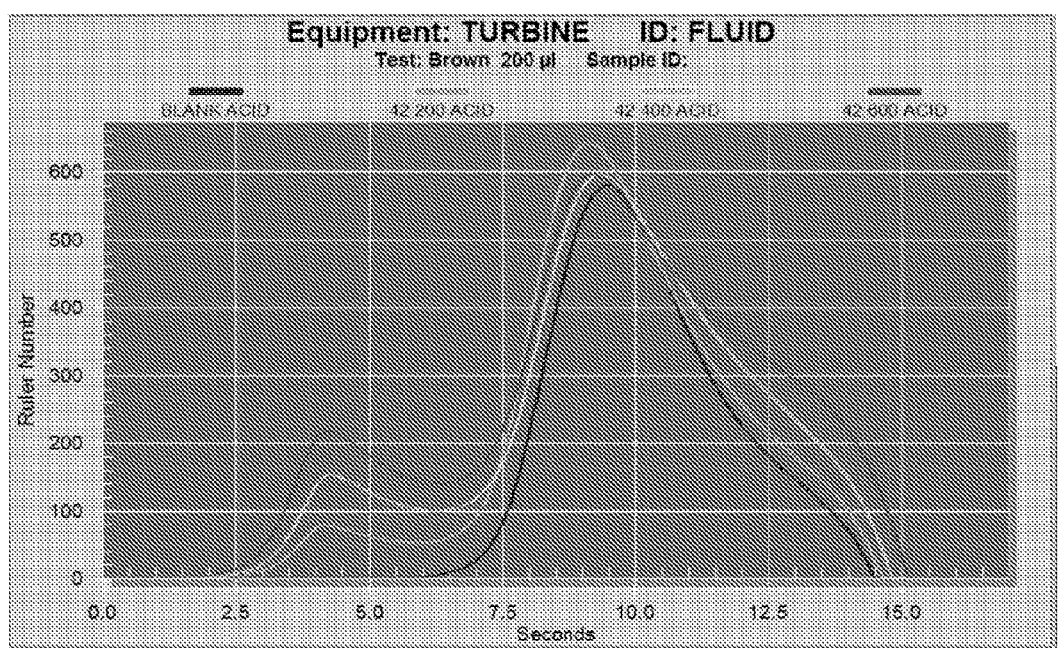
FIG. 7 depicts voltammograms produced by 200-600 μL of used turbine oil with QSA rating 42 added to sodium phenate in alcohol solution (no HCl added).

Since the QSA 42 sample was the only used oil sample with significant hindered phenol antioxidant content (peak at 14 seconds in FIG. 4), the sample was also analyzed with the alcoholic solution containing sodium phenate. The 42 200 ACID voltammogram in FIG. 7 (200 μL sample size) has a sharp peak at 4 seconds and an increased phenate peak compared to the baseline (phenate peak increase due to peak at 4 seconds). As the sample size is increased to 600 μL in FIG. 7, the front peak at 4 seconds increases with sample size, the phenate peak is stable and only a minimal shoulder forms at 14-15 seconds (varnish/carboxylic acid not present).

Figure 8:
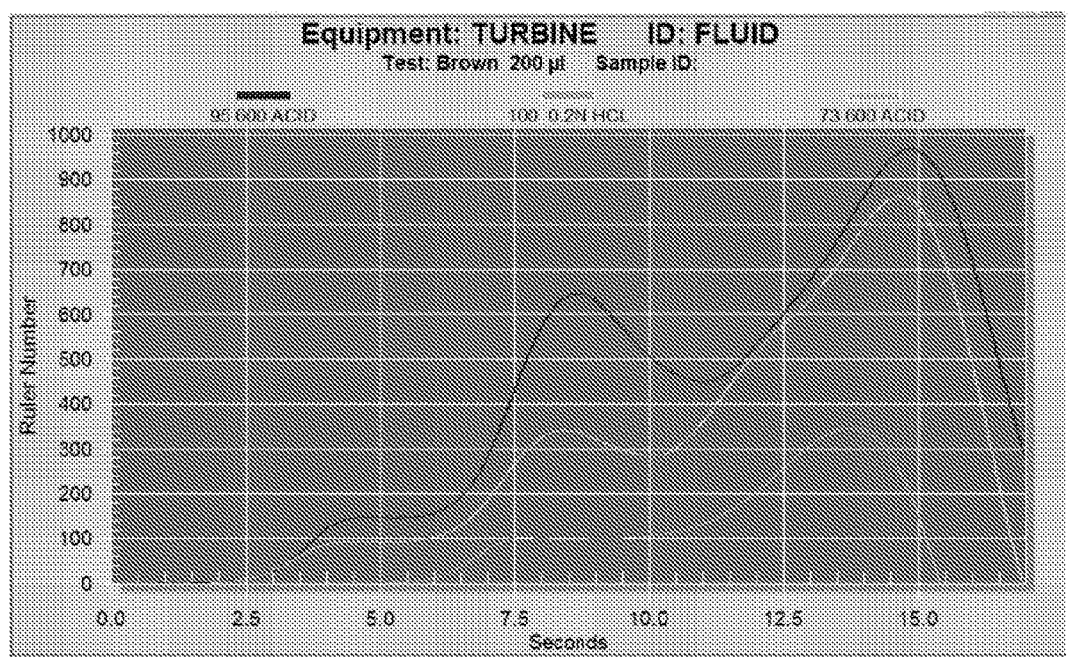
FIG. 8 depicts voltammograms produced by sodium phenate in alcohol solution with 600 μL of used turbine oils with QSA ratings of 73 and 95 (no HCl added) and by 100 μL of 2N HCl.

For an approximate calibration, 100 μL of aqueous 0.2 N HCl was added to a fresh sodium phenate solution and the voltammogram in FIG. 8 shows that the phenate is neutralized by the HCl to produce a phenol peak (14 seconds) that is much smaller than the peaks between 13-17 seconds produced by 600 μL of the used oil samples with QSA ratings of 95 and 73. The 73 and 95 600 ACID voltammograms have similar sized peaks between 13-17 seconds but the sodium phenate peak at 8.5 seconds is reduced to a greater extent for the 73 QSA sample than for the 95 QSA sample, i.e., the 73 QSA sample has a much higher acid content than the 95 QSA sample. The phenol peak produced by the HCl (100 0.2N HCl) is shifted to the left in FIG. 8 in comparison to the amine peak at 14-17 seconds for the 73 and 95 QSA samples, i.e., phenol peak responsible for the larger shoulder at 12 seconds in the 73 600 ACID voltammogram. Both the 73 and 95 600 ACID voltammograms have peaks in the 3-6 second range, i.e., both samples contain sludge with the voltammetric peak size and QSA ratings in agreement, 95 600 Acid>73 600 Acid in FIG. 8.

Example 5

As one final test, 50 μL 2N HCl was added to the normal (QSA 3 and 42) and abnormal (QSA 60 and 64) used turbine oils diluted in ethanol solution containing sodium phenate to determine the type of secondary aromatic amine antioxidants present. In each case, a voltammetric peak was produced in the 11-17 second range (similar to FIG. 8) indicating that the oils contained DODPA type antioxidants and confirming the oils did not contain acidic compounds (produced phenol would have resulted in voltammetric peak in the 11-17 second range as in FIG. 8 without addition of acid).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed:

1. A method of analyzing an oil sample for acidic oxidation products and sludge comprising:
   a. generating a first graphical representation by analyzing a solution of overbased phenate dissolved in alcohol using linear sweep voltammetry;
   b. adding an oil sample to the alcohol solution and analyzing the solution using linear sweep voltammetry to generate a second graphical representation, wherein the second graphical representation comprises peaks corresponding to acidic oxidation products and sludge;
   c. comparing the first graphical representation and the peaks of the second graphical representation.

2. The method of claim 1, further comprising adding an additional sample of oil to the solution one or more times to generate one or more additional graphical representations; and comparing the peaks of the graphical representations.

3. The method of claim 1, wherein the ratio of sample to solution containing overbased phenate is from about 1:5 to about 1:25.

4. The method of claim 1, wherein the overbased phenate is sodium phenate.

5. The method of claim 1, wherein the oil is a lubricating oil.

* * * * *